(12) United States Patent
Matsumoto et al.

(10) Patent No.: US 11,603,514 B2
(45) Date of Patent: Mar. 14, 2023

(54) CELL TREATMENT APPARATUS (71) Applicant: KATAOKA CORPORATION, Kyoto (JP)

(72) Inventors: Junichi Matsumoto, Kyoto (JP); Norihiro Yamagishi, Kyoto (JP)

(73) Assignee: Kataoka Corporation, Kyoto (JP)

(*) Notice: Subject to any disclaimer, the term of this patent is extended or adjusted under 35 U.S.C. 154(b) by 314 days.

(21) Appl. No.: 16/627,108

(22) PCT Filed: May 30, 2019

(86) PCT No.: PCT/JP2019/021620
§ 371 (c)(1),
(2) Date: Dec. 27, 2019

(87) PCT Pub. No.: WO2020/003884
PCT Pub. Date: Jan. 2, 2020

(65) Prior Publication Data
US 2021/0363475 A1 Nov. 25, 2021

(30) Foreign Application Priority Data
Jun. 29, 2018 (JP) .............................. JP2018-124722

(51) Int. Cl.
C12M 1/00 (2006.01)
C12M 1/42 (2006.01)
C12M 1/34 (2006.01)

(52) U.S. Cl.
CPC ............ C12M 23/34 (2013.01); C12M 35/02 (2013.01); C12M 41/36 (2013.01); C12M 47/04 (2013.01)

(58) Field of Classification Search
CPC ...... C12M 23/34; C12M 41/36; C12M 35/02; C12M 47/04
(Continued)

(56) References Cited

U.S. PATENT DOCUMENTS 7,754,478 B2 * 7/2010 Suzuki ................... C12M 23/22
435/303.3
2003/0148393 A1 8/2003 Woodbury
(Continued)

FOREIGN PATENT DOCUMENTS

EP 3 467 091 4/2019
WO 2004/037968 5/2004
(Continued)

OTHER PUBLICATIONS

Tateno H., et al.. "Elimination of Tumorigenic Human Pluripotent Stem Cells by a RecombinantLectin-Toxin Fusion Protein", Stem Cell Reports, vol. 4, Issue 5, pp. 811-820.
(Continued)

Primary Examiner — Michael L Hobbs
Assistant Examiner — Lenora A Abel
(74) Attorney, Agent, or Firm — Hamre, Schumann, Mueller & Larson, P.C.

(57) ABSTRACT

The present invention provides a cell treatment apparatus that can improve the operating rates of an observation unit and a laser irradiation unit in the case of treating a plurality of cell culture vessels. The cell treatment apparatus of the present invention includes: a cell treatment chamber in which cells in a cell culture vessel are treated; an observation unit that can observe the cells in the cell culture vessel; a laser irradiation unit that can irradiate the cells with lasers; a first moving unit that can move the observation unit; and a second moving unit that can move the laser irradiation unit, wherein the cell treatment chamber includes a plurality of regions in which the cells can be treated, each region includes a first cell culture vessel placement unit and a second cell culture vessel placement unit, in the first cell culture vessel placement unit, the cells in the cell culture vessel are observed by the observation unit, in the second
(Continued)

cell culture vessel placement unit, the cells in the cell culture vessel are irradiated with lasers by the laser irradiation unit, the observation unit is moved by the first moving unit in a state of being able to observe the cells in the cell culture vessel in the first cell culture vessel placement unit of each region, and the laser irradiation unit is moved by the second moving unit in a state of being able to irradiate the cells in the cell culture vessel in the second cell culture vessel placement unit of each region with lasers.

9 Claims, 5 Drawing Sheets (58) Field of Classification Search
USPC .................................................. 435/294.1
See application file for complete search history.

(56) References Cited

U.S. PATENT DOCUMENTS

| 2005/0276456 | A1 | 12/2005 | Yamato |
| 2008/0057558 | A1 | 3/2008 | Niwa et al. |
| 2013/0023025 | A1 | 1/2013 | Sumaru |
| 2014/0287452 | A1 | 9/2014 | Sugiyama et al. |
| 2015/0044770 | A1 | 2/2015 | Kim |
| 2016/0103072 | A1* | 4/2016 | Fukutake ............... C12M 21/08 435/29 |
| 2017/0342439 | A1 | 11/2017 | Saito et al. |

FOREIGN PATENT DOCUMENTS

| WO | 2006/088154 | 8/2006 |
| WO | 2013/069452 | 5/2013 |
| WO | 2014/162744 | 10/2014 |
| WO | 2016/010119 | 1/2016 |
| WO | 2017/208589 | 12/2017 |
| WO | 2018/047702 | 3/2018 |
| WO | 2018/088245 | 5/2018 |

OTHER PUBLICATIONS

International Search report and Written Opinion issued in PCT/JP2019/021620, dated Aug. 13, 2019, 11 pages.

Office Action issued in U.S. Appl. No. 15/576,228, filed Oct. 7, 2019, 11 pages.

* cited by examiner

CELL TREATMENT APPARATUS

TECHNICAL FIELD

The present invention relates to a cell treatment apparatus.

BACKGROUND ART

In regenerative medicine, in order to produce cells of a cell sheet or the like, tissues, organs, and the like, there is a need to culture large quantities of cells. When the large quantities of cells are cultured, non-target cells are produced in addition to target cells. Thus, it is necessary to remove the non-target cells during or after culturing the large quantities of cells.

Examples of the method of removing the non-target cells include a method of using a substance having a high specificity for the non-target cells (Non Patent Literature 1) and a method of introducing mRNAs encoding apoptotic genes controlled to be expressed only in the specific cells (Patent Literature 1). However, in any of the methods, there is a problem that the non-target cells cannot be completely removed.

CITATION LIST

Patent Literature

Patent Literature 1: WO 2016/010119

Non Patent Literature

Non Patent Literature 1: Hiroaki Tateno et. al., "Elimination of Tumorigenic Human Pluripotent Stem Cells by a Recombinant Lectin-Toxin Fusion Protein", Stem Cell Reports, Volume 4, Issue 5, pages 811-820

SUMMARY OF INVENTION

Technical Problem

Hence, the inventors of the present invention have invented a cell treatment apparatus including: an observation unit that can observe cells in a cell culture vessel; and a laser irradiation unit that can irradiate the cells in the cell culture vessel with lasers, as a new apparatus that can treat the non-target cells, such as killing or removing the cells. In the cell treatment apparatus, the cells in the cell culture vessel are observed by the observation unit, and the target cells or non-target cells are identified. Then, the laser irradiation unit is used to treat the non-target cells.

However, in the cell treatment apparatus, when the observation unit is in operation, the laser irradiation unit is not in operation, and conversely, when the laser irradiation unit is in operation, the observation unit is not in operation. Thus, a problem has been found that in the case of treating a plurality of cell culture vessels, either the observation unit or the laser irradiation unit waits to treat, which causes a decrease in the operation rates.

With the foregoing in mind, it is an object of the present invention to provide a cell treatment apparatus that can improve the operating rates of an observation unit and a laser irradiation unit when treating a plurality of cell culture vessels.

Solution to Problem

In order to achieve the above object, the present invention provides a cell treatment apparatus including:

a cell treatment chamber in which cells in a cell culture vessel are treated;
an observation unit that can observe the cells in the cell culture vessel;
a laser irradiation unit that can irradiate the cells with lasers;
a first moving unit that can move the observation unit; and
a second moving unit that can move the laser irradiation unit, wherein
the cell treatment chamber includes a plurality of regions in which the cells can be treated,
each region includes a first cell culture vessel placement unit and a second cell culture vessel placement unit,
in the first cell culture vessel placement unit, the cells in the cell culture vessel are observed by the observation unit,
in the second cell culture vessel placement unit, the cells in the cell culture vessel are irradiated with lasers by the laser irradiation unit,
the observation unit is moved by the first moving unit in a state of being able to observe the cells in the cell culture vessel in the first cell culture vessel placement unit of each region, and
the laser irradiation unit is moved by the second moving unit in a state of being able to irradiate the cells in the cell culture vessel in the second cell culture vessel placement unit of each region with lasers.

Advantageous Effects of Invention

According to the present invention, it is possible to improve the operating rates of an observation unit and a laser irradiation unit in the case of treating a plurality of cell culture vessels.

DESCRIPTION OF EMBODIMENTS

Hereinafter, in the present invention, the "X-axis direction" refers to the longitudinal direction of a cell treatment chamber on the bottom surface of a cell treatment chamber, the "Y-axis direction" refers to the direction orthogonal to the X-axis direction on the bottom surface, and the "Z-axis direction" refers to the direction perpendicular (orthogonal) to the bottom surface.

In the present invention, "treatment of cells" refers to treatment of cells such as cell killing, removal of unwanted cells by liberation or the like from a cell culture vessel, selection of wanted cells, and shape-processing or the like of aggregates of cells such as a cell sheet, an organ, and the like.

The cell treatment apparatus of the present invention is described in detail below with reference to the drawings. It is to be noted, however, that the present invention is by no means limited or restricted by the following description. Note that the same reference signs may be given to the same components in FIGS. 1 to 5 below and descriptions thereof may be omitted. Furthermore, for convenience in explanation, the structure of each component shown in the drawings may be appropriately simplified, and the size, the ratio, and the like of components may be schematically shown and different from actual ones. Regarding the descriptions of the embodiments, reference can be made to each other unless otherwise stated.

First Embodiment

Figure 1:
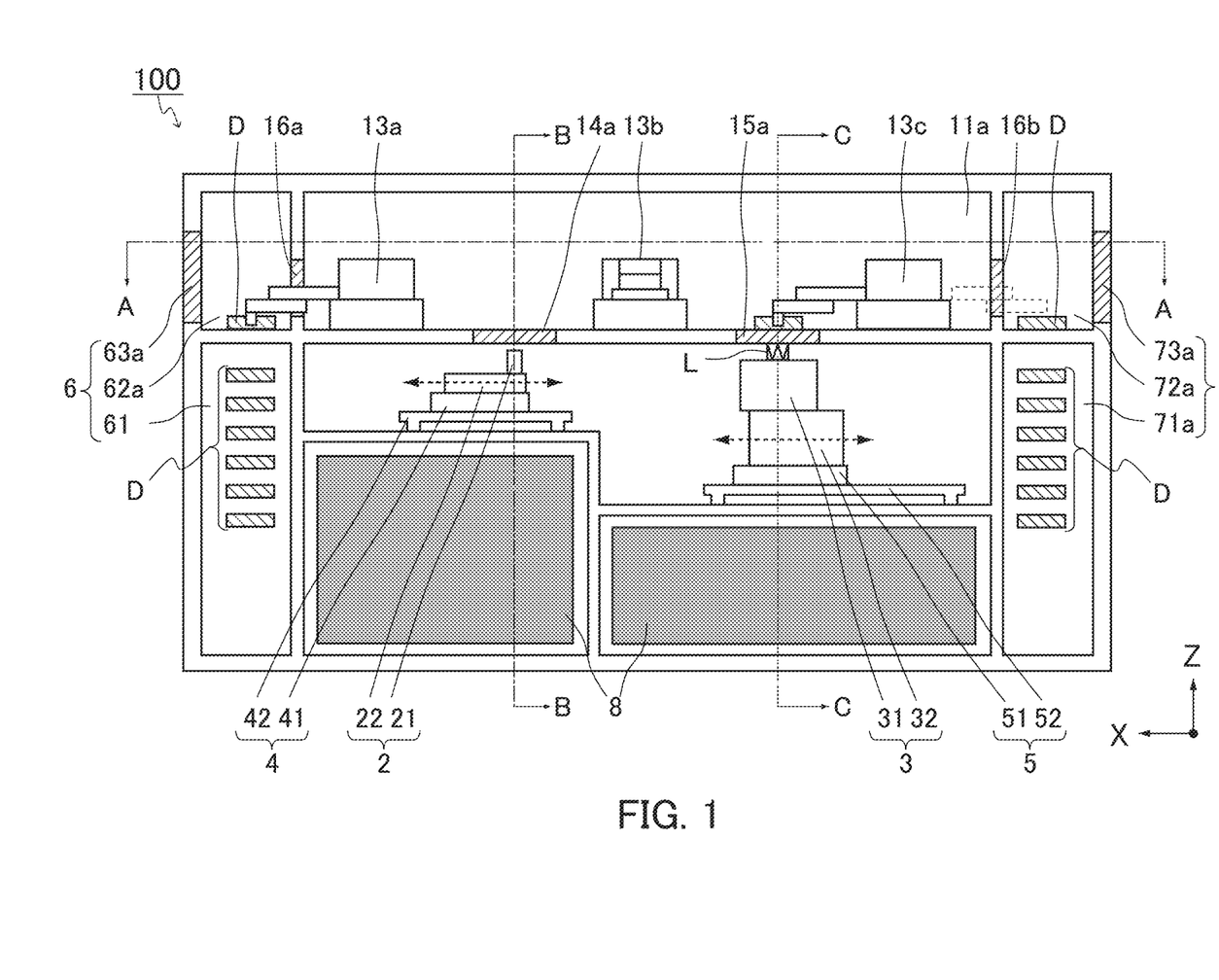
FIG. 1 is a schematic cross-sectional view showing an example of a cell treatment apparatus according to the first embodiment.
Figure 2:
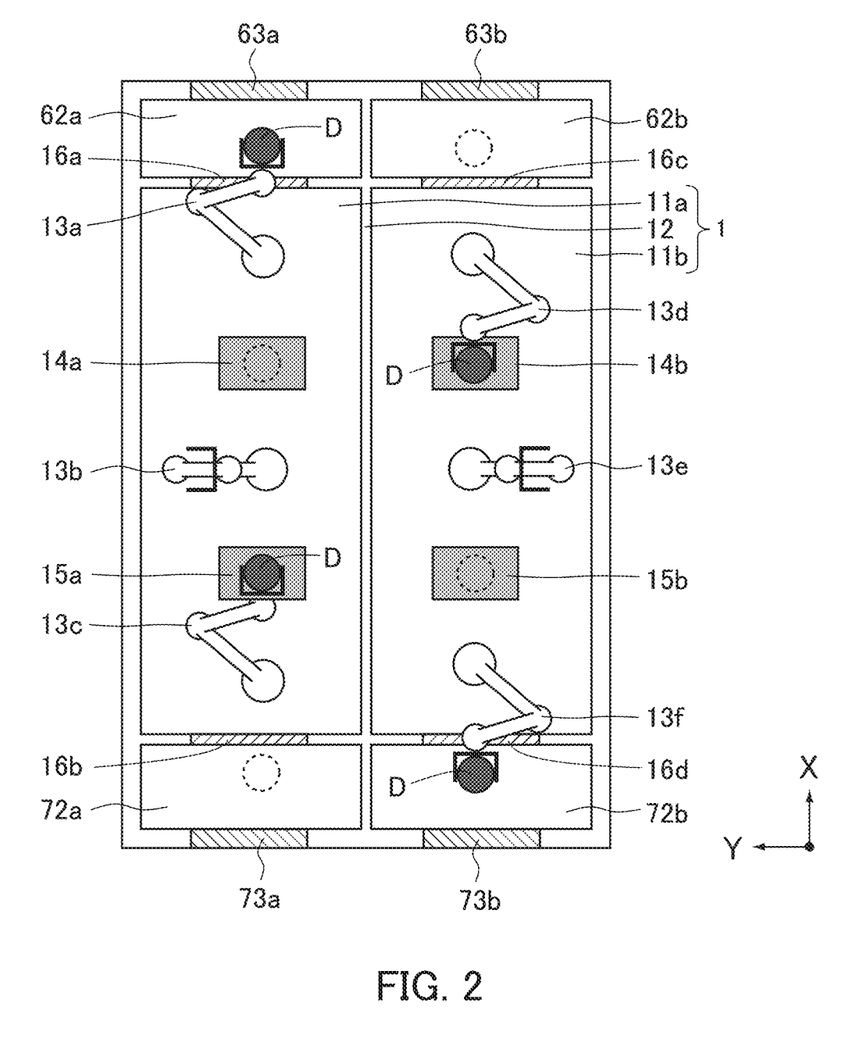
FIG. 2 is a schematic cross-sectional view showing an example of a cell treatment apparatus according to the first embodiment.
Figure 3:
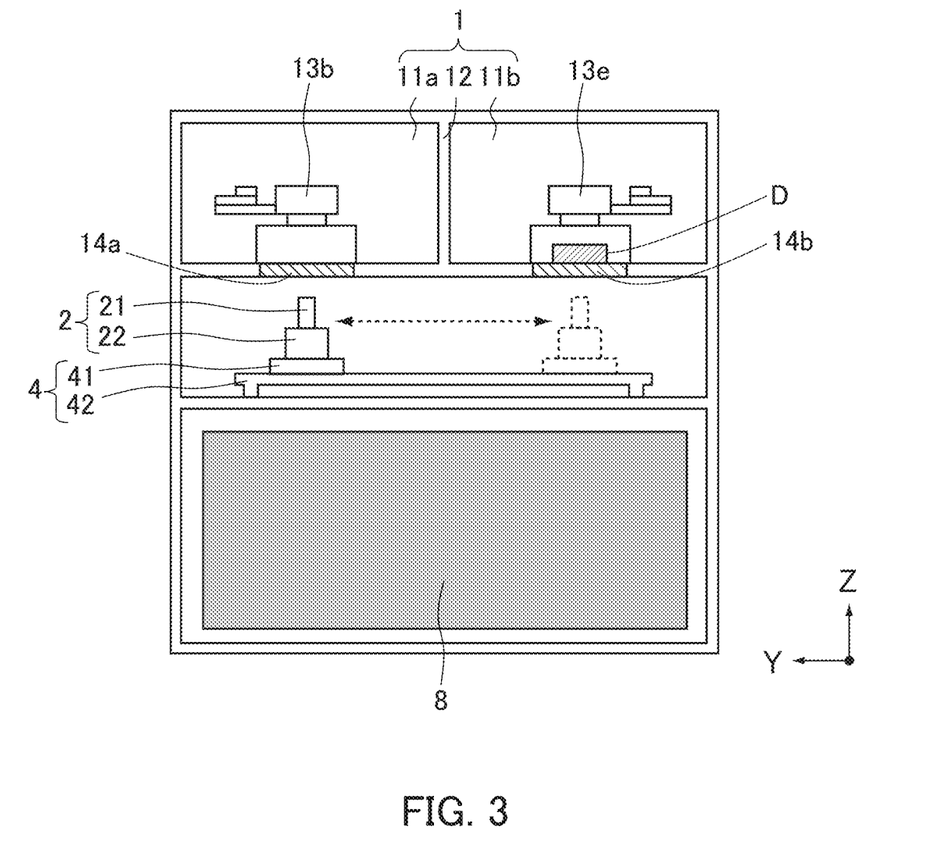
FIG. 3 is a schematic cross-sectional view showing an example of a cell treatment apparatus according to the first embodiment.
Figure 4:
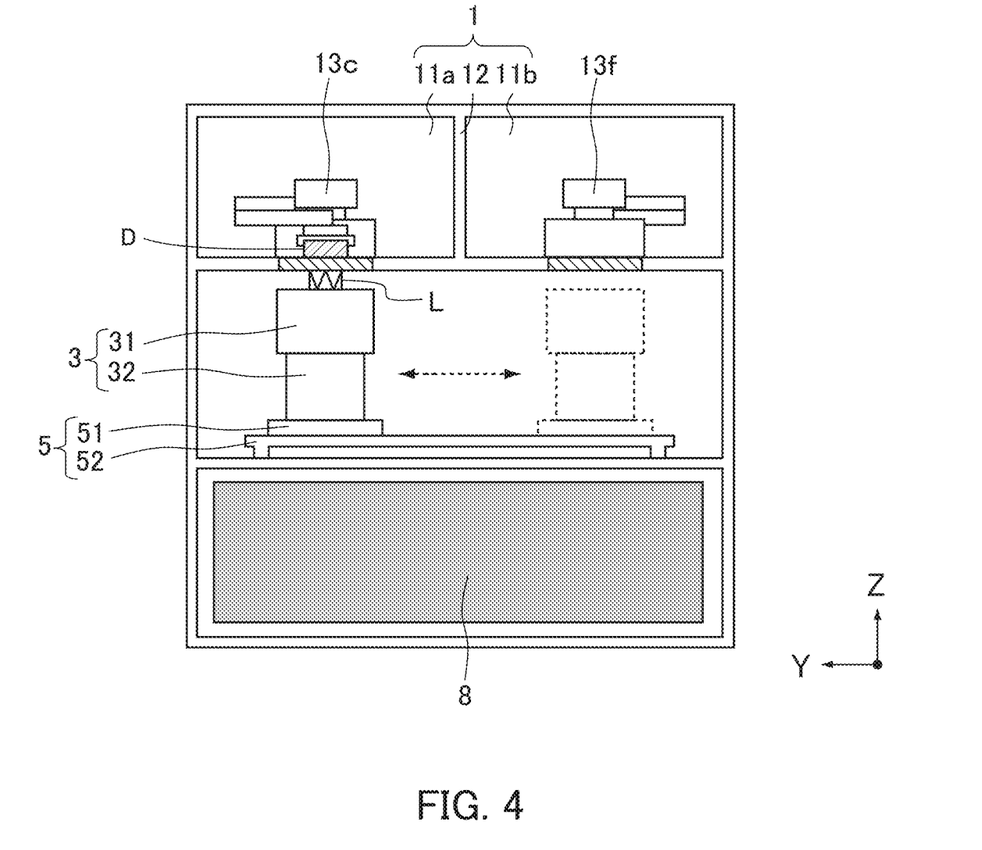
FIG. 4 is a schematic cross-sectional view showing an example of a cell treatment apparatus according to the first embodiment.

The present embodiment shows an example of a cell treatment apparatus. FIG. 1 is a schematic cross-sectional view of a cell treatment apparatus 100 according to the first embodiment viewed from the side. FIG. 2 is a schematic cross-sectional view taken along the line A-A in FIG. 1. FIG. 3 is a schematic cross-sectional view taken along the line B-B in FIG. 1. FIG. 4 is a schematic cross-sectional view taken along the line C-C in FIG. 1. As shown in FIGS. 1 and 2, the cell treatment apparatus 100 includes a cell treatment chamber 1, an observation unit 2, a laser-treating unit 3, a first moving unit 4, a second moving unit 5, a supply unit 6, a reclaim unit 7, and a control unit 8 as main components. A plurality of cell culture vessels D are accommodated in the cell treatment apparatus 100. The cell culture vessels D include cell culture vessels before being treated and cell culture vessels after being treated. However, in the cell treatment apparatus 100 of the present embodiment, the supply unit 6, the reclaim unit 7, the control unit 8, and the cell culture vessel D are optional and the cell treatment apparatus 100 may or may not include any one or more of them. The cell treatment apparatus 100 preferably includes both the supply unit 6 and the reclaim unit 7 because they allow the process to be automated.

The cell treatment chamber 1 is a chamber in which cells in the cell culture vessel D are treated. As shown in FIG. 2, in the present embodiment, the cell treatment chamber 1 has a first cell treatment region 11a and a second cell treatment region 11b. The first cell treatment region 11a and the second cell treatment region 11b are separated (isolated) by a wall 12 so that the air in both regions is not mixed. Thus, when different cells such as cells from different humans, cells from different animals, and cells of different types are treated in the respective regions in the cell treatment chamber 1, mixing of different cells can be prevented, and different cells can be treated with one cell treatment apparatus 100. While the cell treatment chamber 1 has two cell treatment regions in the present embodiment, the cell treatment chamber 1 is only required to have a plurality of cell treatment regions. The wall 12 is optional and the cell treatment chamber 1 may or may not include the wall 12.

The first cell treatment region 11a and the second cell treatment region 11b are regions in which the cells can be treated. As shown in FIG. 2, the first cell treatment region 11a and the second cell treatment region 11b linearly include: first cell culture vessel placement units 14a and 14b in which the cells in the cell culture vessels D can be observed by the observation unit 2; and second cell culture vessel placement units 15a and 15b in which the cells in the cell culture vessels D can be irradiated with lasers by the laser-treating unit 3, respectively. Each of the first cell treatment region 11a and the second cell treatment region 11b forms an independent treatment lane. Thus, the first cell treatment region 11a and the second cell treatment region 11b may be also referred to as, for example, a first cell treatment lane and a second cell treatment lane. The circles indicated by the broken lines in the first cell culture vessel placement unit 14a and the second cell culture vessel placement unit 15b in FIG. 2 show examples of locations where the cell culture vessel D is placed. In the first cell treatment region 11a and the second cell treatment region 11b, for example, since the first cell culture vessel placement units 14a and 14b and the second cell culture vessel placement units 15a and 15b are placed linearly, the observation and the treatment of the cells in the cell culture vessels D can be performed by moving the cell culture vessels D in the X-axis direction, which allows prompt treatment of the cells in the cell culture vessels D. It is to be noted that, the placement of the first cell culture vessel placement units 14a and 14b and the second cell culture vessel placement units 15a and 15b is not limited , and they can be placed at any position, respectively, in the first cell treatment region 11a and the second cell treatment region 11b. Since the cell treatment chamber 1 can prevent the inflow of undesired substances such as dust and the like from the outside of the cell treatment chamber 1, for example, it is preferable that a connecting portion connected to the outside of the cell treatment chamber 1 be sealed by a sealing compound such as a packing, a sealing member, or the like. The material for forming the cell treatment chamber 1 may be, for example, stainless-steel. The cell treatment chamber 1 is preferably sterilizable by, for example, hydrogen peroxide, UV light, or the like.

The first cell treatment region 11a includes SCARA robots 13a, 13b, and 13c, which are vessel transfer units, a first cell culture vessel placement unit 14a, and a second cell culture vessel placement unit 15a. The first cell treatment region 11a includes openable and closable openings 16a and 16b on the walls at both ends in the X-axis direction, respectively, and the first cell treatment region 11a is connected to the supply unit 6 and the reclaim unit 7 through the openings 16a and 16b, respectively. The second cell treatment region 11b includes SCARA robots 13d, 13e, and 13f, which are vessel transfer units, a first cell culture vessel placement unit 14b, and a second cell culture vessel placement unit 15b. The second cell treatment region 11b includes openings 16c and 16d on the walls at both ends in the X-axis direction, respectively, and the second cell treatment region 11b is connected to the supply unit 6 and reclaim unit 7 through the openings 16c and 16d, respectively. Preferably, the openings 16a, 16b, 16c, and 16d are configured to be openable and closable by providing a door, for example. As a result, undesired substances such as dust and the like can be prevented from flowing into the first cell treatment region 11a and the second cell treatment region 11b. The openings 16a, 16b, 16c, and 16d are optional and the first and second cell treatment regions 11a and 11b may or may not include the openings 16a, 16b, 16c, and 16d, however, when the cell treatment apparatus 100 includes at least one of the supply unit 6 and the reclaim unit 7, the first and second cell treatment regions 11a and 11b preferably have openings through which they are connected to the supply unit 6 and the reclaim unit 7.

In each of the first cell culture vessel placement units 14a and 14b, cells in the cell culture vessels D are observed by the observation unit 2. Thus, the first cell culture vessel placement units 14a and 14b can also be referred to as observation portions, for example. While each of the first cell culture vessel placement units 14a and 14b is formed as a light-transmitting portion on the bottom surface of the cell treatment chamber 1 (the lower surface of the first cell treatment region 11a in FIG. 1) in the present embodiment, the first cell culture vessel placement units 14a and 14b only require that the cells in the cell culture vessel D can be observed by the observation unit 2. The first cell culture vessel placement units 14a and 14b are composed, for example, of a member (light-transmitting member) that transmits the light to be observed by the observation unit 2. When the observation unit 2 is an optical microscope, examples of the light-transmitting member include a transparent glass plate and an acrylic plate. Each of the first cell culture vessel placement units 14a and 14b may have a recess in which the cell culture vessel D can be placed, for example.

In each of the second cell culture vessel placement units 15a and 15b, the laser irradiation unit 3 irradiates the cells in the cell culture vessel D with lasers. Thus, the second cell culture vessel placement units 15a and 15b can also be referred to as laser-treating portions, for example. While each of the second cell culture vessel placement units 15a and 15b is formed as a laser light-transmitting portion on the bottom surface of the cell treatment chamber 1 (the lower surface of the first cell treatment region 11a in FIG. 1) in the present embodiment, the second cell culture vessel placement units 15a and 15b only require that the cells in the cell culture vessel D can be irradiated with lasers by the laser irradiation unit 3. The second cell culture vessel placement units 15a and 15b are composed, for example, of a member (laser light-transmitting member) that transmits the laser light irradiated by the laser irradiation unit 3. Examples of the laser light-transmitting member include a transparent glass plate and an acrylic plate. Each of the second cell culture vessel placement units 15a and 15b may have a recess in which the cell culture vessel D can be placed, for example. While the first cell culture vessel placement units 14a and 14b and the second cell culture vessel placement units 15a and 15b are the same in shape, size, forming materials, and the like in the present embodiment, they may be different in shape, size, forming materials, and the like.

While the vessel transfer units are SCARA robots 13a to 13f in the present embodiment, the vessel transfer unit only is required to be able to transfer the cell culture vessel D. The vessel transfer unit may be, for example, a contact type or non-contact type conveying device. Specifically, the contact type conveying device may be, for example, a conveyor. The non-contact type conveying device may be, for example, a conveying device using magnetism such as MagTran®. In the present embodiment, the SCARA robots 13a and 13d collect the cell culture vessels D provided to the pass boxes 62a and 62b of the supply unit 6 described below across the openings 16a and 16c and place them in the first cell culture vessel placement units 14a and 14b, respectively. The SCARA robots 13b and 13e collect the cell culture vessels D that have been observed by the observation unit 2 from the first cell culture vessel placement units 14a and 14b and place them in the second cell culture vessel placement units 15a and 15b, respectively. The SCARA robots 13c and 13f collect the cell culture vessels D that have been laser-treated by the laser irradiation unit 3 from the second cell culture vessel placement units 15a and 15b and place them in the pass boxes 72a and 72b of the reclaim unit 7 across the openings 16b and 16d, respectively.

In the present embodiment, the cell culture vessel D is not particularly limited, and may be, for example, a culture vessel such as a well-known dish, a flask, or the like used for cell culture. The material for forming the cell culture vessel D is not particularly limited, and may be, for example, a material that transmits a laser image projected by a laser projection unit to be described below, and specific examples thereof include plastics and glasses that transmit lasers. Examples of the plastic include polystyrene polymers, acrylic polymers (polymethyl methacrylate (PMMA) and the like), polyvinylpyridine polymers (poly(4-vinylpyridine), 4-vinylpyridine-styrene copolymers and the like), silicone polymers (polydimethylsiloxane and the like), polyolefin polymers (polyethylene, polypropylene, polymethylpentene and the like), polyester polymers (polyethylene terephthalate (PET), polyethylene naphthalate (PEN), and the like), polycarbonate polymers, and epoxy polymers.

The cell culture vessel D preferably includes, for example, a laser absorbing layer formed of a polymer (photoresponsive material) including a dye structure (chromophore) that absorbs laser L, or a laser absorbing layer formed of a photoacid generator that absorbs the laser L and generates an acidic material, on the bottom surface of the inside of the cell culture vessel D (the bottom surface side of the cells in FIG. 1). As to the dye structure and the photoacid generator, reference can be made to, for example, the description of Japanese Patent No. 6033980. Since the cell culture vessel D includes the laser absorbing layer, the energy of the laser can be converted into heat, acid, or the like when the laser irradiation unit 3 of the cell treatment apparatus 100 irradiates the cells in the cell culture vessel D with lasers, for example, thereby killing, releasing, or the like the cells present above the laser absorbing layer.

The cell may be a cell, a cell mass composed of cells, a tissue, an organ, or the like.

The cell may be, for example, a cultured cell or a cell isolated from a living body. The cell mass, the tissue, or the organ may be, for example, a cell mass, a cell sheet, a tissue, or an organ produced from the cells, or may be a cell mass, a tissue, or an organ isolated from a living body.

While the observation unit 2 includes the imaging optical system 21 and the imaging unit 22 in the present embodiment, the observation unit 2 is only required to observe the cells in the cell culture vessel D. Furthermore, while the observation unit 2 is placed below the cell culture vessel D in the present embodiment, the observation unit 2 may be placed above the cell culture vessel D. In the latter case, the observation unit 2 is placed, for example, in the cell treatment chamber 1. The imaging unit 22 includes, for example, an image sensor including a Charge-Coupled Device (CCD), a Complementary Metal Oxide Semiconductor (CMOS), and the like. The observation unit 2 may be, for example, an optical microscope, an electronic microscope, or the like. Examples of the optical microscope include a phase-contrast microscope, a differential interference contrast microscopy, a polarization microscopy, a fluorescence microscope, a confocal laser scanning microscope, a total internal reflection fluorescence microscope, and a Raman microscope. When the observation unit 2 is the optical microscope, the observation unit 2 may include, for example, a light source. The light source is not particularly limited, and can be appropriately determined depending on the type of the optical microscope, and specific examples thereof include halogen lamps, tungsten lamps, and white Light Emitting Diodes (LEDs). The location of the light source is not particularly limited, and can be appropriately determined depending on the type of the optical microscope. As a specific example, the light source may be placed inside of the cell treatment chamber 1. In this case, the light source is placed so as to face the imaging optical system and the image sensor of the observation unit 2 with the cell culture vessel D interposed therebetween, for example, at the time of taking an image by the imaging unit 22. When the observation unit 2 is provided with the light source, the cell treatment apparatus 100 preferably includes, for example, a light source moving unit that can move the light source. The light source moving unit moves the light source so as to be in conjunction with the imaging optical system, the image sensor, and the like of the observation unit 2, for example. Specifically, the light source moving unit moves the light source so that the X-Y coordinate of the imaging optical system and the image sensor of the observation unit 2 coincide with the X-Y coordinate of the light source, for example. The light source moving unit may move the light source before, after, or during moving the observation unit 2 by the first moving unit 4. For example, the observation unit 2 may be configured such that the position information of the observation unit 2 can be acquired. As to the position information, reference can be made, for example, to the description of the position information in the first moving unit 4.

While the laser irradiation unit 3 includes a laser emission unit 31 and a laser light source 32 in the present embodiment, the laser irradiation unit 3 only is required to be able to irradiate cells with the laser L. For example, the laser irradiation unit 3 irradiates the cells determined to be the irradiation target of the laser among the cells observed by the observation unit 2 with the laser L. The laser-irradiation target cells may be determined based on, for example, images of cells in the cell culture vessel D taken by the observation unit 2. While the laser irradiation unit 3 is placed below the cell culture vessel D in the present embodiment, the laser irradiation unit 3 may be placed above the cell culture vessel D. In the latter case, the laser irradiation unit 3 is placed, for example, in the cell treatment chamber 1. The laser L is oscillated by the laser light source 32, for example, and guided to the laser emission unit 31. The laser emission unit 31 and the laser light source 32 are optically connected to each other. While the laser L oscillated from the laser light source 32 is guided to the laser emission unit 31 by optical fibers (not shown) in the present embodiment, the laser emission unit 31 and the laser light source 32 may use a light guiding device such as a mirror, Micro Electro Mechanical Systems (MEMS), or the like to guide the laser L. For example, the laser irradiation unit 3 may be configured such that the position information of the laser irradiation unit 3 can be acquired. As to the position information, reference can be made, for example, to the description of the position information in the second moving unit 5.

The laser emission unit 31 emits the laser L. Specifically, the laser emission unit 31 irradiates, for example, the cells in the cell culture vessel D or the laser absorbing layer with the laser L. In the present embodiment, the irradiation position of the laser L (laser irradiation position) is based on the coordinate in the XY axes of the laser emission unit 31. The laser irradiation position is moved, for example, by moving the laser irradiation unit 3 by the second moving unit 5 to be described below to move the laser emission unit 31. The moving direction of the laser irradiation position (the scanning direction of the laser L) is, for example, a direction from one end of the cell culture vessel D to the other end. The movement of the laser irradiation position in the laser irradiation unit 3 is not limited thereto, and may be performed by an irradiation position moving unit that can move the laser irradiation position. In this case, the laser irradiation unit 3 includes the irradiation position moving unit. Examples of the irradiation position moving unit include a Galvano scanner and a polygon scanner. The laser irradiation unit 3 is provided with a Galvano scanner as the irradiation position moving unit, whereby the cell culture vessel D can be treated with the laser L in a shorter time, and, for example, the treatment time for treating a plurality of cell culture vessels D can be further shortened.

The laser light source 32 is, for example, a device that oscillates a continuous wave laser or a pulsed laser. The laser light source 32 may be, for example, a high-frequency laser having a long pulse width close to a continuous wave. The output of the laser oscillated from the laser light source 32 is not particularly limited, and can be appropriately determined depending on, for example, the treatment and the cells. The wavelength of the laser oscillated by the laser light source 32 is not particularly limited, and can be, for example, a visible light laser, an infrared laser, or the like having a wavelength of 405 nm, 450 nm, 520 nm, 532 nm, 808 nm, or the like. As described above, when the laser absorbing layer is provided in the cell culture vessel D, the laser light source 32 oscillates, for example, the laser having a wavelength that can be absorbed by the laser absorbing layer. Since the influence on cells can be suppressed, it is preferable that the laser light source 32 oscillates a laser having a wavelength longer than 380 nm. The laser output of the laser light source 32 can be set according to, for example, the wavelength of the laser, the spot diameter of the laser, and the moving speed of the laser. When the wavelength of the laser is 405 nm, the spot diameter is 45 and the moving speed of the laser is 80 mm/sec, the output of the laser light source 32 is, for example, 0.4 W or more. As a specific example, when the laser absorbing layer is formed in the cell culture vessel D, the laser light source 32 can be a continuous-wave diode laser having a wavelength in the vicinity of a wavelength of 405 nm and a maximum output of 5 W.

In the present embodiment, while the first moving unit 4 includes a carriage 41 and a X-Y rail 42, the first moving unit 4 only is required to be able to move the observation unit 2 so that the cells in the cell culture vessels D in the first cell culture vessel placement units 14a and 14b of the respective regions can be observed. As the first moving unit 4, for example, a known moving unit (drive unit) can be used. While the moving directions of the first moving unit 4 are the X-axis direction and the Y-axis direction as indicated by the broken line and arrow in FIGS. 1 and 3 in the present embodiment, the moving direction of the first moving unit 4 is not particularly limited, and may be, for example, any one direction, two directions, or all directions of the X-axis direction, the Y-axis direction, and the Z-axis direction. The first moving unit 4 can move the observation unit 2 so that cells in a desired position in a cell culture vessel D can be observed or the image thereof can be taken by the observation unit 2, for example. As described above, when the observation unit 2 includes a light source, the first moving unit 4 may be able to move the light source, i.e., may also serve as the light source moving unit, for example. In this case, the first moving unit 4 may move, for example, the observation unit 2 and the light source by one moving unit. The first moving unit 4 may acquire its position information, for example. Examples of the position information include coordinates (two-dimensional coordinates) in the XY axes and coordinates (three-dimensional coordinates) in the XYZ axes. When the first moving unit 4 acquires the position information, the first moving unit 4 may acquire the position information as the position information of the observation unit 2, for example. The first moving unit 4 is only required to be placed so as to be able to move the observation unit 2, and may be appropriately placed depending on a moving unit to be used, for example. Moving the observation unit 2 by the first moving unit 4 may be controlled by the control unit 8, for example, as described below.

In the present embodiment, while the second moving unit 5 includes a carriage 51 and a XY rail 52, the second moving unit 5 only is required to be able to move the laser irradiation unit 3 so that the cells in the cell culture vessels D in the second cell culture vessel placement units 15a and 15b of the respective regions can be irradiated with the laser light L. As the second moving unit 5, for example, a known moving unit (drive unit) can be used. While the second moving unit 5 can move the entire laser irradiation unit 3, the second moving unit 5 may be able to move a part of the laser irradiation unit 3. In this case, the second moving unit 5 can move the laser emission unit 31, for example. While the moving directions of the second moving unit 5 are the X-axis direction and the Y-axis direction as indicated by the broken line and arrow in FIGS. 1 and 4 in the present embodiment, the moving direction of the second moving unit 5 is not particularly limited, and may be, for example, any one direction, two directions, or all directions of the X-axis direction, the Y-axis direction, and the Z-axis direction. The second moving unit 5 can move the laser irradiation unit 3 so that cells in a desired position in a cell culture vessel D can be irradiated with lasers, for example. The second moving unit 5 may, for example, acquire its position information. Examples of the position information include coordinates (two-dimensional coordinates) in the XY axes, and coordinates (three-dimensional coordinates) in the XYZ axes. When the second moving unit 5 acquires the position information, the second moving unit 5 may acquire the position information as the position information of the laser irradiation unit 3, for example. The second moving unit 5 is only required to be placed so as to be able to move the laser irradiation unit 3, and may be appropriately placed depending on a moving unit to be used, for example. Moving the laser irradiation unit 3 by the second moving unit 5 may be controlled by the control unit 8, for example, as described below.

In the present embodiment, the first moving unit 4 and the second moving unit 5 are configured as independent units. That is, the first moving unit 4 and the second moving unit 5 are configured to be able to independently move the observation unit 2 and the laser irradiation unit 3, respectively. Thereby, during the observations by the observation unit 2 or the lasing by the laser irradiation unit 3, the unit not under operation can be moved so that the operating rates of the observation unit 2 and the laser irradiation unit 3 can be further improved. It is to be noted that the cell treatment apparatus of the present invention is not limited thereto, and the first moving unit 4 and the second moving unit 5 may be configured as a single unit, for example.

While the observation unit 2, the laser irradiation unit 3, the first moving unit 4, and the second moving unit 5 are placed in one chamber in the present embodiment, they may be placed in separate chambers. The placement of the first moving unit 4 and the second moving unit 5 can be appropriately determined depending on the placement and configuration of the observation unit 2 and the laser irradiation unit 3.

While the supply unit 6 includes a stacker 61 and pass boxes 62a and 62b in the present embodiment, the supply unit 6 is only required to be able to provide the cell culture vessel D. By providing the stacker 61 and path boxes 62a and 62b, the inflow of undesired substances such as dust and the like from the outside of the cell treatment chamber 1 can be prevented at the time of supplying the cell culture vessel D. The pass boxes 62a and 62b of the supply unit 6 have openable and closable openings 63a and 63b, respectively. This allows a user of the cell treatment apparatus 100 to maintain, for example, the inside of the cell treatment apparatus 100. The stacker 61 can, for example, accommodate a plurality of cell culture vessels D and supply the culture vessels D to the cell treatment chamber 1. Specifically, the stacker 61 supplies one or more cell culture vessels D to the pass boxes 62a and 62b. In FIG. 2, the circle indicated by the broken line in the pass box 62b indicates a location to which the cell culture vessel D is supplied by the stacker 61. While one stacker 61 supplies the cell culture vessels D to the pass boxes 62a and 62b in the present embodiment, separate stackers 61 may be provided to supply the cell culture vessels D to the pass boxes 62a and 62b. The supply unit 6 may be, for example, a combination of an incubator that can accommodate the cell culture vessel D therein and a conveying device for the cell culture vessel D. The supply unit 6 may have the incubation function of the cell culture vessel D, for example. In this case, the supply unit 6 includes, for example, a temperature regulating unit, a pH regulating unit, a humidity regulating unit, an oxygen concentration regulating unit, and the like. The temperature adjusting unit may be, for example, a heating unit such as a heater. The pH regulating unit may be, for example, a carbon dioxide concentration regulating unit or the like, and as a specific example, the pH regulating unit may be a connecting portion connected to a carbon dioxide supply unit outside the cell treatment apparatus 100. The humidity regulating unit may be, for example, a humidification tray or the like. The oxygen concentration regulating unit may be, for example, a nitrogen concentration regulating unit or the like, and as a specific example, the oxygen concentration regulating unit may be a connecting portion connected to a nitrogen supply unit outside the cell treatment apparatus 100.

While the reclaim unit 7 includes a reclaimer 71 and pass boxes 72a and 72b in the present embodiment, the reclaim unit 7 is only required to reclaim the cell culture vessel D being treated. By providing a reclaimer 71 and pass boxes 72a and 72b, the inflow of undesired substances such as dust and the like from the outside of the cell treatment chamber 1 can be prevented at the time of reclaiming the cell culture vessel D. The pass boxes 72a and 72b of the reclaim unit 7 have openable and closable openings 73a and 73b, respectively. This allows a user of the cell treatment apparatus 100 to maintain, for example, the inside of the cell treatment apparatus 100. The reclaimer 71 can, for example, reclaim and accommodate the cell culture vessel D that has been treated in the cell treatment chamber 1. Specifically, the reclaimer 71 reclaims one or more cell culture vessels D transferred into the pass boxes 72a and 72b after being treated by the laser irradiation unit 3. In FIG. 2, the circle indicated by the broken line in the pass box 72a indicates a location to which the cell culture vessel D after being treated is supplied. While one reclaimer 71 reclaims the cell culture vessels D in the pass boxes 72a and 72b in the present embodiment, separate reclaimers 71 may be provided to reclaim the cell culture vessels D in the pass boxes 72a and 72b. The reclaim unit 7 may be, for example, a combination of an incubator that can accommodate the cell culture vessel D therein and a conveying device for the cell culture vessel D. The reclaim unit 7 may have the incubation function of the cell culture vessel D, for example. In this case, the reclaim unit 7 includes, for example, the above-described temperature regulating unit, pH regulating unit, humidity regulating unit, oxygen concentration regulating unit, and the like.

While the cell treatment apparatus 100 includes the control unit 8 in the present embodiment, the control unit 8 is optional and the cell treatment apparatus 100 may or may not include the control unit 8. If the cell treatment apparatus 100 does not include the control unit 8, the units of the cell treatment apparatus 100 may be controlled by a control device such as, for example, a personal computer, a server computer, a workstation, or the like outside the cell treatment apparatus 100.

Figure 5:
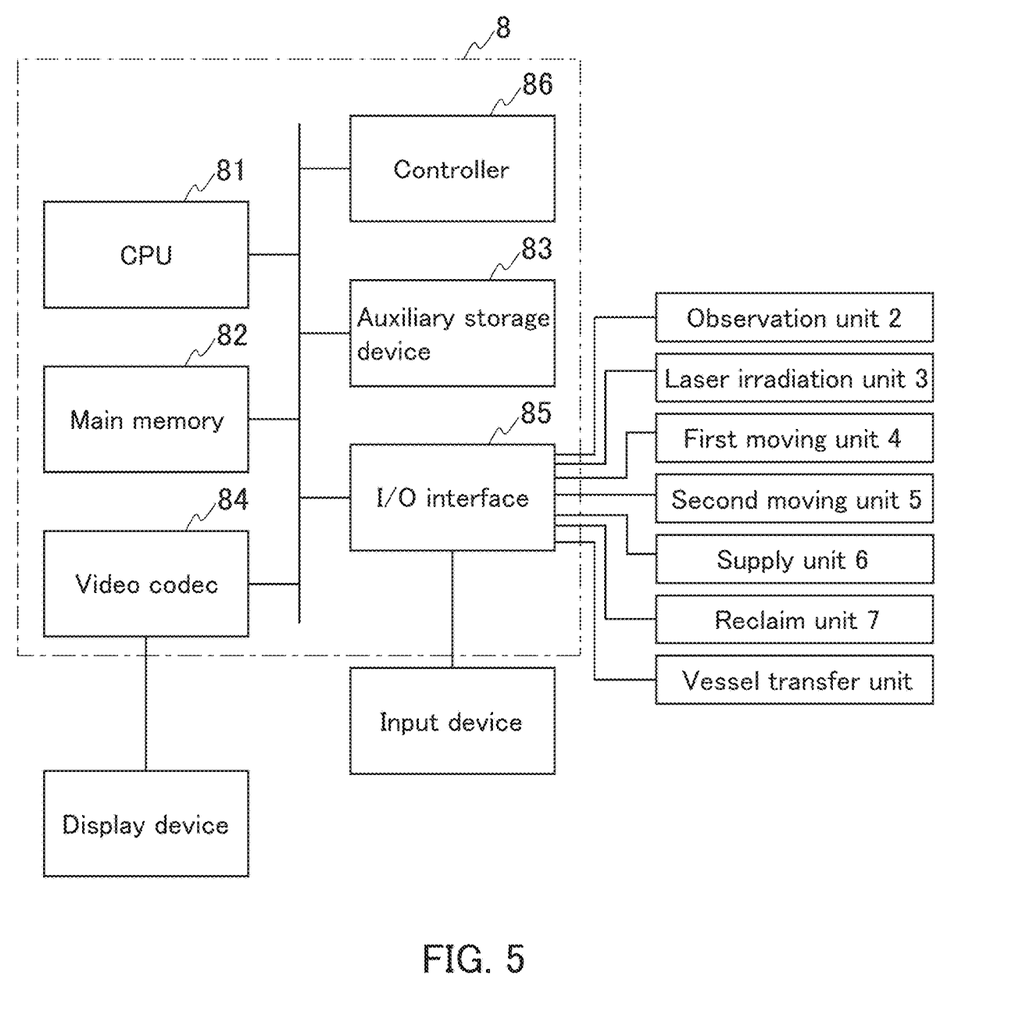
FIG. 5 is a block diagram showing a control unit in the cell treatment apparatus according to the first embodiment.

The control unit 8 includes a configuration similar to a personal computer, a server computer, a workstation, or the like. FIG. 5 is a block diagram showing an example of a control unit 8 in the cell treatment apparatus 100 according to the present embodiment. As shown in FIG. 5, the control unit 5 includes a central processing unit (CPU) 81, a main memory 82, an auxiliary storage device 83, a video codec 84, an input-output (I/O) interface 85, and the like, which are controlled by a controller (a system controller, an I/O controller, or the like) 86 and operate in cooperation with each other. The auxiliary storage device 83 can be a storage device such as a flash memory and a hard disk drive. The video codec 84 includes: a graphics processing unit (GPU) that generates a screen to be displayed based on a drawing instruction received from the CPU 81 and transmits the screen signal to a display device or the like outside the cell treatment apparatus 100; and a video memory that temporarily stores the screen and image data, for example. The I/O interface 85 is a device that can communicate with and control the units such as the observation unit 2, the laser irradiation unit 3, the first moving unit 4, the second moving unit 5, the supply unit 6, the reclaim unit 7, and the vessel transfer units (SCARA robots 13*a* to 13*f*). The I/O interface 85 may include a servo driver (servo controller). The I/O interface 85 may be connected to an input unit (input device) outside the cell treatment apparatus 100, for example. The display device may be, for example, monitors (for example, various image display devices such as a liquid crystal display (LCD) and a cathode ray tube (CRT) display) which output images. Examples of the input device include a touch panel, a track pad, a pointing device such as a mouse, a keyboard, and a push button which can be operated by a finger of a user.

The programs executed by the control unit 8 and the respective pieces of information are stored in the auxiliary storage device 83. The program is read into the main memory 82 at the time of executing the program and is decoded by the CPU 81. The control unit 8 controls each unit according to the program.

The control unit 8 controls the observation of cells in the cell culture vessel D by the observation unit 2, for example. Specifically, the control unit 8 controls, for example, ON/OFF of imaging an image by the imaging unit 22 in the observation unit 2, taking an image, ON/OFF of the light source, and the like. When the observation unit 2 captures an image, the control unit 8 may acquire the position information of the observation unit 2 at the time of imaging, for example. In this case, the control unit 8 may associate the taken image with the position information, for example. When the observation unit 2 takes an image, the control unit 8 may determine, for example, whether the cells in the obtained image are laser-irradiation targets. For example, the control unit 8 may store the obtained images in the memory 82. The determination method is not particularly limited, and may be a method of determining using a learned model obtained by performing depth learning of a laser-irradiation target cell or a laser-irradiation non-target cell. The determination may be performed, for example, by a user of the cell treatment apparatus 100 inputting using the input device.

The control unit 8 controls, for example, the irradiation of the cells in the cell culture vessel D with lasers by the laser irradiation unit 3. Specifically, the control unit 8 controls, for example, ON/OFF of the laser irradiation by the laser irradiation unit 3, the change of the irradiation position of the laser, and the like. When the laser irradiation unit 3 includes the irradiation position moving unit, the control unit 8 may control the irradiation position moving unit to control the irradiation position of the laser, for example. The control unit 8 may acquire the position information of the laser irradiation unit 3.

The control unit 8 controls, for example, the movement of the observation unit 2 by the first moving unit 4. Specifically, the control unit 8 controls the movement of the observation unit 2 by the first moving unit 4, for example, so that the observation unit 2 is placed at a position where desired cells can be observed. The control unit 8 may control the movement of the observation unit 2 by the first moving unit 4 by, for example, specifying the position information of the destination of the observation unit 2. The control unit 8 may acquire the position information of the first moving unit 4.

The control unit 8 controls, for example, the movement of the laser irradiation unit 3 by the second moving unit 5. Specifically, the control unit 8 controls the movement of the laser irradiation unit 3 by the second moving unit 5, for example, so that the laser irradiation unit 3 is placed at a position where desired cells can be irradiated with lasers. The control unit 8 may control the movement of the laser irradiation unit 3 by the second moving unit 5 by, for example, specifying the position information of the destination of the laser irradiation unit 3. The control unit 8 may acquire the position information of the second moving unit 5.

The control unit 8 controls, for example, the supply of the cell culture vessel D by the supply unit 6. Specifically, when there is no cell culture vessel D in the path boxes 62*a* and 62*b*, the control unit 8 supplies the cell culture vessels D in the stacker 61 to the path boxes 62*a* and 62*b*, for example. The control unit 8 may control, for example, to supply the cell culture vessels D in the stacker 61 to the pass boxes 62*a* and 62*b* after the cell culture vessels D in the pass boxes 62*a* and 62*b* are transferred by the SCARA robots 13*a* and 13*d* to the first cell culture vessel placement units 14*a* and 14*b*.

The control unit 8 controls, for example, reclaiming the cell culture vessel D by the reclaim unit 7. Specifically, when there are cell culture vessels D in the pass boxes 72*a* and 72*b*, the control unit 8 reclaims the cell culture vessels D from the pass boxes 72*a* and 72*b* into the reclaimer 71, for example. The control unit 8 may control the reclaimer 71 to reclaim the cell culture vessels D in the pass boxes 72*a* and 72*b* after the cell culture vessel D is transferred from the second cell culture vessel placement units 15*a* and 15*b* into the pass boxes 72*a* and 72*b* by the SCARA robots 13*c* and 13*f*, for example.

The control unit 8 controls, for example, the transfer of the cell culture vessel D by the vessel transfer unit. Specifically, the control unit 8 controls, for example, the transfer (placement) of the cell culture vessels D to the first cell culture vessel placement units 14*a* and 14*b*, the transfer (placement) of the cell culture vessels D to the second cell culture vessel placement units 15*a* and 15*b*, and the transfer (removal) of the cell culture vessels D from the second cell culture vessel placement units 15*a* and 15*b*. In the present embodiment, the control unit 8 controls the transfer of the cell culture vessels D from the pass boxes 62*a* and 62*b* to the first cell culture vessel placement units 14*a* and 14*b* by the SCARA robots 13*a* and 13*d*. The control unit 8 controls the transfer of the cell culture vessels D from the first cell culture vessel placement units 14*a* and 14*b* to the second cell culture vessel placement units 15*a* and 15*b* by the SCARA robots 13*b* and 13*e*. Further, the control unit 8 controls the transfer of the cell culture vessels D from the second cell culture vessel placement units 15*a* and 15*b* to the pass boxes 72*a* and 72*b* by the SCARA robots 13*c* and 13*f*.

The control unit 8 may control the opening and closing of the openings 16*a* to 16*d* if the openings 16*a* to 16*d* are openable and closable, for example. Specifically, the control unit 8 may control to open the openings 16*a* to 16*d* before the passage of the cell culture vessels D through the openings 16*a* to 16*d* and to close the openings 16*a* to 16*d* after the passage of the cell culture vessels D.

In the cell treatment apparatus 100 of the present embodiment, the control unit 8 has the function of controlling the observation unit 2, the laser irradiation unit 3, the first moving unit 4, the second moving unit 5, the supply unit 6, and the reclaim unit 7, so that a control unit does not have to be individually provided in each unit, whereby the device can be miniaturized. However, the present invention is not limited thereto. In the cell treatment apparatus of the present invention, for example, a control unit as the control unit 8 may be provided in each of the observation unit 2, the laser irradiation unit 3, the first moving unit 4, the second moving unit 5, the supply unit 6, and the reclaim unit 7, and each unit may be controlled by the control unit of each unit. The cell treatment apparatus of the present invention may include, for example, the control unit 8 and the control units of the respective units to control the units in cooperation. The control unit 8 may be configured by one semiconductor element, may be a chip in which a plurality of semiconductor elements are packaged, or may be a substrate on which a plurality of semiconductor elements are provided.

The cell treatment apparatus 100 of the present embodiment may include, for example, a power supply unit. The power supply unit supplies power to each unit, for example. The power supply unit is not particularly limited, and a known power supply can be used.

The cell treatment apparatus 100 of the present embodiment may include, for example, an air supply unit for supplying a gas such as carbon dioxide or oxygen to the cell culture vessel D of each cell treatment region (for example, the first cell treatment region 11*a* and the second cell treatment region 11*b*). The air supply unit may be, for example, a connecting portion connected to a gas supply unit (e.g., a gas cylinder) outside the cell treatment apparatus 100. This makes it possible to suppress the variation of the culture condition of the cells when the cells in the cell culture vessels D are treated in the respective cell treatment regions. The cell treatment apparatus 100 of the present embodiment may include, for example, an exhaust unit for exhausting the gas in the cell culture vessel D of each cell treatment region (for example, first cell treatment region 11*a* and second cell treatment region 11*b*). The exhaust unit may be, for example, a connecting portion connected to the outside of the cell treatment apparatus 100. As a result, the cell treatment apparatus 100 of the present embodiment can suppress the variation of the culture condition of the cells when the cells in the cell culture vessels D are treated in the respective cell treatment regions.

The cell culture vessel D may have identifiers that can identify the respective cell culture vessels D. Examples of the identifier include a QR code®, a bar code, a stamp, a print, and a marker. The cell culture vessel D may have the identifier prior to the treatment in the cell treatment apparatus 100, or the identifier may be given to the cell culture vessel D during treatment in the cell treatment apparatus 100. In the latter case, the identifier of the cell culture vessel D may be formed using, for example, a laser irradiation device having the same configuration as the laser irradiation unit 3, or may be formed by attaching a sticking member such as a sticker having the identifier encoded thereon using a sticking device. The identifiers may be formed, for example, for the cell culture vessels D placed in the first cell culture vessel placement units 14*a* and 14*b*, or may be formed for the cell culture vessels D before being placed in the first cell culture vessel placement units 14*a* and 14*b*. In the former case, the laser irradiation device, an identifier forming device such as the sticking device, or the like is placed so as to be able to form identifiers on the cell culture vessels D in the first cell treatment region 11*a* and the second cell treatment region 11*b* of the cell culture apparatus 100, for example. The identifier forming device may be located, for example, above each of the first cell culture vessel placement units 14*a* and 14*b* in the first cell treatment region 11*a* and the second cell treatment region 11*b*. In the latter case, the first cell treatment region 11*a* of the cell culture apparatus 100 may be provided with an identifier forming region in which the cell culture vessels D can be placed between the pass box 62*a* and the first cell culture vessel placement unit 14*a*, and the second cell treatment region 11*b* of the cell culture apparatus 100 may be provided with an identifier forming region in which the cell culture vessels D can be placed between the pass box 62*b* and the first cell culture vessel placement unit 14*b*. The identifier forming device is placed in each of the first cell treatment region 11*a* and the second cell treatment region 11*b* of the cell culture apparatus 100 so as to be able to form an identifier on the cell culture vessel D, for example. The identifier forming device may be located, for example, above the identifier forming region. In the case where the cell culture vessel D has an identifier, the cell treatment apparatus 100 of the present embodiment preferably has an identification unit that identifies the identifier of the cell culture vessel D. The identification unit may be, for example, a combination of an imaging device such as a camera and a data-processing unit (control unit 8) for decoding the identifiers. If the identification unit is provided, it is preferable that the cell treatment apparatus 100 store images observed or taken by the observation unit 2 and the identifiers in association with each other. The identification unit is placed in each of the first cell treatment region 11*a* and the second cell treatment region 11*b* so as to be able to identify the cell culture vessel D placed in each of the first cell culture vessel placement units 14*a* and 14*b* and the second cell culture vessel placement units 15*a* and 15*b*. If the identification unit is an imaging device, the imaging device is placed, for example, above each of the first cell culture vessel placement units 14*a* and 14*b* and the second cell culture vessel placement units 15*a* and 15*b*.

The cell treatment apparatus 100 of the present embodiment may include a position adjusting unit for aligning the positions and angles of the cell culture vessels D in the second cell culture vessel placement units 15*a* and 15*b* with the positions and angles of the cell culture vessels D in the first cell culture vessel placement units 14*a* and 14*b* based on the identifiers of the cell culture vessels D. The position adjusting unit may align only the positions of the cell culture vessels D, may align only the angles of the cell culture vessels D, or may align the both of them. In the cell treatment apparatus 100 of the present embodiment, the cell culture vessels D are observed by the observation unit 2 in the first cell culture vessel placement units 14*a* and 14*b*, and then the cell culture vessels D are transferred to the second cell culture vessel placement units 15*a* and 15*b*. Thus, the orientation (e.g., angle) of the cell culture vessel D may change during its transfer. The cell treatment apparatus 100 of the present embodiment includes a position adjusting unit, whereby the positions and angles of the cell culture vessels D in the first cell culture vessel placement units 14*a* and 14*b* can be aligned with the positions and angles of the cell culture vessels D in the second cell culture vessel placement units 15*a* and 15*b*. Therefore, according to the cell treatment apparatus 100 including the position adjusting unit, for example, even in the case of treating the inside of the cell culture vessel D with lasers after being observed by the observation unit 2, the positional deviation of the laser treatment can be suppressed at the time of performing the laser treatment by the laser irradiation unit 3. The position adjusting unit includes: for example, a data processing unit (control unit) for detecting the position (for example, the position in the X-Y coordinate) and the angle of the cell culture vessel D using the image obtained by the imaging device; and a position and angle adjusting unit for adjusting the detected position and angle. For example, the above-described SCARA robots 13*b*, 13*c*, 13*e*, and 13*f* can be used as the position and angle adjusting unit.

In the cell treatment apparatus 100 of the present embodiment, the control unit 8 may adjust the scanning direction of the laser L of the laser irradiation unit 3 based on the identifier of the cell culture vessel D. In this case, the control unit 8 adjusts the scanning direction of the laser L based on, for example, the identifiers of the cell culture vessels D placed in the first cell culture vessel placement units 14*a* and 14*b* and the identifiers of the cell culture vessels D placed in the second cell culture vessel placement units 15*a* and 15*b*. Specifically, the control unit 8 identifies (detects) by the identification unit, for example, the position of the identifier of the cell culture vessel D placed in each of the first cell culture vessel placement units 14*a* and 14*b* and the position of the identifier of the cell culture vessel D placed in each of the second cell culture vessel placement units 15*a* and 15*b*, and detects, on the basis of the positions of the two identifiers, the rotational angle caused when the cell culture vessel D is transferred from each of the first cell culture vessel placement units 14*a* and 14*b* to each of the second cell culture vessel placement units 15*a* and 15*b*. For example, the control unit 8 rotates the scanning direction of the laser L determined on the basis of the image taken by the observation unit 2 or the XY axes of the laser emission unit 31 in accordance with the detected rotational angle. This allows the control unit 8 to adjust the scanning direction of the laser L of the laser irradiation unit 3. The adjustment of the scanning direction of the laser L may be combined with the position adjusting unit.

Next, the method of treating cells using the cell treatment apparatus 100 of the present embodiment is described below.

First, the control unit 8 supplies the cell culture vessel D from the stacker 61 of the supply unit 6 to the pass box 62*a*. Next, the control unit 8 transfers the cell culture vessel D in the pass box 62*a* to the first cell culture vessel placement unit 14*a* by the SCARA robot 13*a*. After transferring the cell culture vessel D, the control unit 8 may supply another cell culture vessel D from the stacker 61 of the supply unit 6 to the pass box 62*a*.

Next, the control unit 8 determines, for example, whether the observation unit 2 is in operation. If the observation unit 2 is in operation, the control unit 8 stops transferring the cell culture vessel D placed in the first cell culture vessel placement unit 14*a* until the observation (taking an image) by the observation unit 2 is finished, for example. If the observation by the observation unit 2 is finished, the control unit 8 moves the observation unit 2 below the first cell culture vessel placement unit 14*a* by the first moving unit 4, and observes the cells in the cell culture vessel D. On the other hand, if the observation unit 2 is not in operation, the control unit 8 moves the observation unit 2 below the first cell culture vessel placement unit 14*a* by the first moving unit 4 and observes the cells in the cell culture vessel D. The control unit 8 determines the laser-irradiation target cells in the taken images. Next, the control unit 8 transfers the cell culture vessel D after being observed from the first cell culture vessel placement unit 14*a* to the second cell culture vessel placement unit 15*a* by the SCARA robot 13*b*. After transferring the cell culture vessel D, the control unit 8 determines whether the cell culture vessel D is present in the pass box 62*a*. If the cell culture vessel D is present in the path box 62*a*, the control unit 8 may transfer the cell culture vessel D in the path box 62*a* to the first cell culture vessel placement unit 14*a* by the SCARA robot 13*a*.

Next, the control unit 8 determines, for example, whether the laser irradiation unit 3 is in operation. When the laser irradiation unit 3 is in operation, the control unit 8 stops transferring the cell culture vessel D placed in the second cell culture vessel placement unit 15*a* until the laser irradiation by the laser irradiation unit 3 is finished, for example. When the laser irradiation by the laser irradiation unit 3 is finished, the control unit 8 moves the laser irradiation unit 3 below the second cell culture vessel placement unit 15*a* by the second moving unit 5, and irradiates the irradiation target cells in the cell culture vessel D with lasers. On the other hand, when the laser irradiation unit 3 is not in operation, the control unit 8 moves the laser irradiation unit 3 below the second cell culture vessel placement unit 15*a* by the second moving unit 5, and irradiates the irradiation target cells in the cell culture vessel D with lasers. Next, the control unit 8 transfers the cell culture vessel D after being treated from the second cell culture vessel placement unit 15*a* to the pass box 72*a* of the reclaim unit 7 by the SCARA robot 13*c*. After transferring, the control unit 8 determines whether there is the cell culture vessel D after being observed. When there is the cell culture vessel D after being observed, the control unit 8 may transfer the cell culture vessel D after being observed from the first cell culture vessel placement unit 14*a* to the second cell culture vessel placement unit 15*a* by the SCARA robot 13*b*.

Next, the control unit 8 reclaims the cell culture vessel D in the pass box 72*a* of the reclaim unit 7 into the reclaimer 71. After reclaiming the cell culture vessel D, the control unit 8 determines whether there is the cell culture vessel D after being treated. If there is the cell culture vessel D after being treated, the control unit 8 may transfer the cell culture vessel D after being treated from the second cell culture vessel placement unit 15*a* to the pass box 72*a* of the reclaim unit 7 by the SCARA robot 13*c*.

The method of treating cells in the first cell treatment region 11*a* of the cell treatment apparatus of the present embodiment has been described above. Regarding the method of treating cells in the second cell treatment region 11*b*, reference can be made to the description as to the first cell treatment region 11*a* by replacing "SCARA robot 13*a*" with "SCARA robot 13*d*", "SCARA robot 13*b*" with "SCARA robot 13*e*", "SCARA robot 13*c*" with "SCARA robot 13*f*", "first cell culture vessel placement unit 14*a*" with "first cell culture vessel placement unit 14*b*", "second cell culture vessel placement unit 15*a*" with "second cell culture vessel placement unit 15*b*", "pass box 62*a*" with "pass box 62*b*", and "pass box 72*a*" with "pass box 72*b*".

Generally, the time of observing or taking an image of cells in the cell culture vessel D by the observation unit 2 is determined, for example, depending on the size of the cell culture vessel D. On the other hand, the time of irradiating the cells with lasers by the laser irradiation unit 3 varies greatly depending on the quantity of the laser-irradiation target cell in the cell culture vessel D, for example, because the irradiation is performed by a laser close to a point. Therefore, in the case where there is a plurality of regions in which cells can be treated, if the observation unit 2 and the laser irradiation unit 3 are placed in each region, for example, the time in which the observation unit 2 and the laser irradiation unit 3 are not in operation is increased, so that the operating rates of the observation unit 2 and the laser irradiation unit 3 are lowered. In the cell treatment apparatus 100 of the present embodiment, the observation unit 2 and the laser irradiation unit 3 for use in observation and laser irradiation are shared in the respective regions, the positions where observation and laser irradiation are performed in the respective regions are separated, and the observation unit 2 and the laser irradiation unit 3 can be moved across the respective regions by the first moving unit 4 and the second moving unit 5, respectively. Thus, in the cell treatment apparatus 100, after the observation by the observation unit 2 or the laser irradiation by the laser irradiation unit 3 in one region is finished, the observation by the observation unit 2 or the laser irradiation by the laser irradiation unit 3 can be performed in another region. Therefore, according to the cell treatment apparatus 100 of the present embodiment, the operating rates of the observation unit 2 and the laser irradiation unit 3 can be improved. In addition, since the cell treatment apparatus 100 of the present embodiment can improve the operation rates, for example, the treatment time when treating a plurality of cell culture vessels can be shortened, and a large amount of cell culture vessels D can be treated in a shorter time. Furthermore, when the laser-irradiation targets in the cell culture vessel D are specified after being observed by the observation unit 2, for example, a time for analyzing the image obtained by the observation unit 2 is required. In the cell treatment apparatus 100 of the present embodiment, since the cell culture vessels D are transferred to the second cell culture vessel placement units 15*a* and 15*b* after being observed in the first cell culture vessel placement units 14*a* and 14*b*, it is possible to secure a time for analyzing the image obtained by the observation unit 2. Thus, the cell treatment apparatus 100 of the present embodiment can be suitably used, for example, when the inside of the cell culture vessel D is treated with lasers after being observed by the observation unit 2.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2018-124722 filed on Jun. 29, 2018. The entire subject matter of the Japanese Patent Applications is incorporated herein by reference.

<Supplementary Notes>

A part of or the whole of the above-described embodiments and examples can be described as the following supplementary notes. However, the present invention is by no means limited thereto.

(Supplementary Note 1)

A cell treatment apparatus including:

a cell treatment chamber in which cells in a cell culture vessel are treated;

an observation unit that can observe the cells in the cell culture vessel;

a laser irradiation unit that can irradiate the cells with lasers;

a first moving unit that can move the observation unit; and a second moving unit that can move the laser irradiation unit, wherein the cell treatment chamber includes a plurality of regions in which the cells can be treated, each region includes a first cell culture vessel placement unit and a second cell culture vessel placement unit, in the first cell culture vessel placement unit, the cells in the cell culture vessel are observed by the observation unit, in the second cell culture vessel placement unit, the cells in the cell culture vessel are irradiated with lasers by the laser irradiation unit, the observation unit is moved by the first moving unit in a state of being able to observe the cells in the cell culture vessel in the first cell culture vessel placement unit of each region, and the laser irradiation unit is moved by the second moving unit in a state of being able to irradiate the cells in the cell culture vessel in the second cell culture vessel placement unit of each region with lasers.

(Supplementary Note 2)

The cell treatment apparatus according to Supplementary Note 1, wherein the laser irradiation unit includes an irradiation position moving unit that can move a laser irradiation position.

(Supplementary Note 3)

The cell treatment apparatus according to Supplementary Note 2, wherein the irradiation position moving unit is a Galvano scanner.

(Supplementary Note 4)

The cell treatment apparatus according to any one of Supplementary Notes 1 to 3, wherein the first moving unit and the second moving unit can independently move the observation unit and the laser irradiation unit, respectively.

(Supplementary Note 5)

The cell treatment apparatus according to any one of Supplementary Notes 1 to 4, wherein positions of the first cell culture vessel placement unit and the second cell culture vessel placement unit in the apparatus are fixed.

(Supplementary Note 6)

The cell treatment apparatus according to any one of Supplementary Notes 1 to 5, wherein the regions are separated by walls.

(Supplementary Note 7)

The cell treatment apparatus according to any one of Supplementary Notes 1 to 6, wherein the cell treatment chamber includes a vessel transfer unit that can transfer the cell culture vessel.

(Supplementary Note 8)
The cell treatment apparatus according to any one of Supplementary Notes 1 to 7, including:
a supply unit that supplies the cell culture vessel.
(Supplementary Note 9)
The cell treatment apparatus according to any one of Supplementary Notes 1 to 8, including:
a reclaim unit that reclaims the cell culture vessel after being treated.
(Supplementary Note 10)
The cell treatment apparatus according to any one of Supplementary Notes 1 to 9, further including:
an identification unit that identifies identifiers of cell culture vessels placed in the first cell culture vessel placement unit and the second cell culture vessel placement unit; and
a control unit that adjusts a scanning direction of a laser of the laser irradiation unit based on the identifier of the cell culture vessel placed in the first cell culture vessel placement unit and the identifier of the cell culture vessel placed in the second cell culture vessel placement unit.

INDUSTRIAL APPLICABILITY

As described above, according to the cell treatment apparatus of the present invention, it is possible to improve the operating rates of an observation unit and a laser irradiation unit in the case of treating a plurality of cell culture vessels. According to the cell treatment apparatus of the present invention, for example, the treatment time when treating a plurality of cell culture vessels can be shortened. Therefore, the present invention is considerably useful in, for example, the life sciences field, the pharmaceutical field, the regenerative medicine field, and the like in which cells, tissues, and the like are treated.

REFERENCE SIGNS LIST

1: cell treatment chamber
11a: first cell treatment region
11b: second cell treatment region
12: wall
13a, b, c, d, e, f: SCARA robot
14a, b: first cell culture vessel placement unit
15a, b: second cell culture vessel placement unit
16a, b, c, and d: opening
2: observation unit
21: imaging optical system
22: imaging unit
3: laser irradiation unit
31: laser emission unit
32: laser light source
4: first moving unit
41: carriage
42: XY stage
5: second moving unit
51: carriage
52: XY stage
6: supply unit
61: stacker
62a, b: pass box
7: reclaim unit
71: reclaimer
72a, b: pass box
8: control unit
81: CPU
82: main memory
83: auxiliary storage device
84: video-codec
85: I/O interface
86: controller
100: cell treatment apparatus

The invention claimed is:
1. A cell treatment apparatus comprising:
a cell treatment chamber in which cells in a cell culture vessel are treated;
an observation unit that can observe the cells in the cell culture vessel;
a laser irradiation unit that can irradiate the cells with lasers;
a first moving unit that can move the observation unit; and
a second moving unit that can move the laser irradiation unit, wherein
the cell treatment chamber comprises a plurality of regions in which the cells are to be treated, the plurality of regions including at least a first region and a second region that are separated from each other by a wall,
both the first region and the second region include a first cell culture vessel placement unit and a second cell culture vessel placement unit,
in the first cell culture vessel placement unit, the cells in the cell culture vessel are observed by the observation unit, and
in the second cell culture vessel placement unit, the cells in the cell culture vessel are irradiated with lasers by the laser irradiation unit,
the observation unit is moved by the first moving unit from a position for observing the cells in the cell culture vessel in the first cell culture vessel placement unit of the first region to a position for observing the cells in the cell culture vessel in the first cell culture vessel placement unit of the second region,
the laser irradiation unit is moved by the second moving unit from a position for irradiating with a laser the cells in the cell culture vessel in the second cell culture vessel placement unit of the first region to a position for irradiating with a laser the cells in the cell culture vessel in the second cell culture vessel placement unit of the second region,
the first cell culture vessel placement unit comprises a member that transmits light to the observation unit, and
the second cell culture vessel placement unit comprises a member that transmits the laser irradiated by the laser irradiation unit.
2. The cell treatment apparatus according to claim 1, wherein the laser irradiation unit comprises an irradiation position moving unit that moves a laser irradiation position.
3. The cell treatment apparatus according to claim 2, wherein the irradiation position moving unit is a Galvano scanner.
4. The cell treatment apparatus according to claim 1, wherein the first moving unit and the second moving unit independently move the observation unit and the laser irradiation unit, respectively.
5. The cell treatment apparatus according to claim 1, wherein positions of the first cell culture vessel placement unit and the second cell culture vessel placement unit in the apparatus are fixed.
6. The cell treatment apparatus according to claim 1, wherein the cell treatment chamber comprises a vessel transfer unit that transfers the cell culture vessel.

7. The cell treatment apparatus according to claim 1, further comprising:
  a conveying device that supplies the cell culture vessel to the cell treatment chamber.

8. The cell treatment apparatus according to claim 1, further comprising:
  a reclaim unit that reclaims the cell culture vessel after being observed and treated.

9. The cell treatment apparatus according to claim 1, further comprising:
  an identification unit that identifies identifiers of cell culture vessels placed in the first cell culture vessel placement unit and the second cell culture vessel placement unit; and
  a control unit that adjusts a scanning direction of a laser of the laser irradiation unit based on the identifier of the cell culture vessel placed in the first cell culture vessel placement unit and the identifier of the cell culture vessel placed in the second cell culture vessel placement unit.

\* \* \* \* \*